United States Patent
Spada et al.

(10) Patent No.: US 7,063,241 B2
(45) Date of Patent: Jun. 20, 2006

(54) DISPENSING TIP

(75) Inventors: Lon T. Spada, Walnut, CA (US); Paul T. Butorac, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/865,055

(22) Filed: Jun. 10, 2004

(65) Prior Publication Data

US 2005/0274744 A1 Dec. 15, 2005

(51) Int. Cl.
*B65D 47/18* (2006.01)
(52) U.S. Cl. .................................... 222/420
(58) Field of Classification Search ................ 222/420
See application file for complete search history.

(56) References Cited

U.S. PATENT DOCUMENTS

| | | | |
|---|---|---|---|
| 4,568,004 A | 2/1986 | Goncalves | |
| 4,739,906 A * | 4/1988 | LoTurco | 222/494 |
| 5,358,151 A | 10/1994 | Strasenburgh | |
| 5,431,314 A * | 7/1995 | Bonnelye et al. | 222/420 |
| 6,105,828 A | 8/2000 | Kanner et al. | |
| 6,129,248 A | 10/2000 | Hagele | |
| 6,197,008 B1 | 3/2001 | Hagele | |
| 6,632,202 B1 | 10/2003 | Hagele | |
| 2002/0084290 A1* | 7/2002 | Materna | 222/420 |
| 2004/0140319 A1* | 7/2004 | Gerondale | 222/420 |

FOREIGN PATENT DOCUMENTS

WO       WO 95/17338 A    6/1995

* cited by examiner

*Primary Examiner*—Philippe Derakshani
(74) *Attorney, Agent, or Firm*—Walter A. Hackler

(57) ABSTRACT

A dispensing tip includes a body suitable for attachment to a dispensing bottle along with a nozzle having a lumen therethrough for flow of liquid formulation and an egress orifice which is in fluid communication with the lumen for the formation of droplets. A concave arcuate surface of revolution about the egress orifice is provided and depending therefrom for enhancing droplet separation from the egress orifice which in turn insures uniform droplet formation and dispensement.

19 Claims, 1 Drawing Sheet

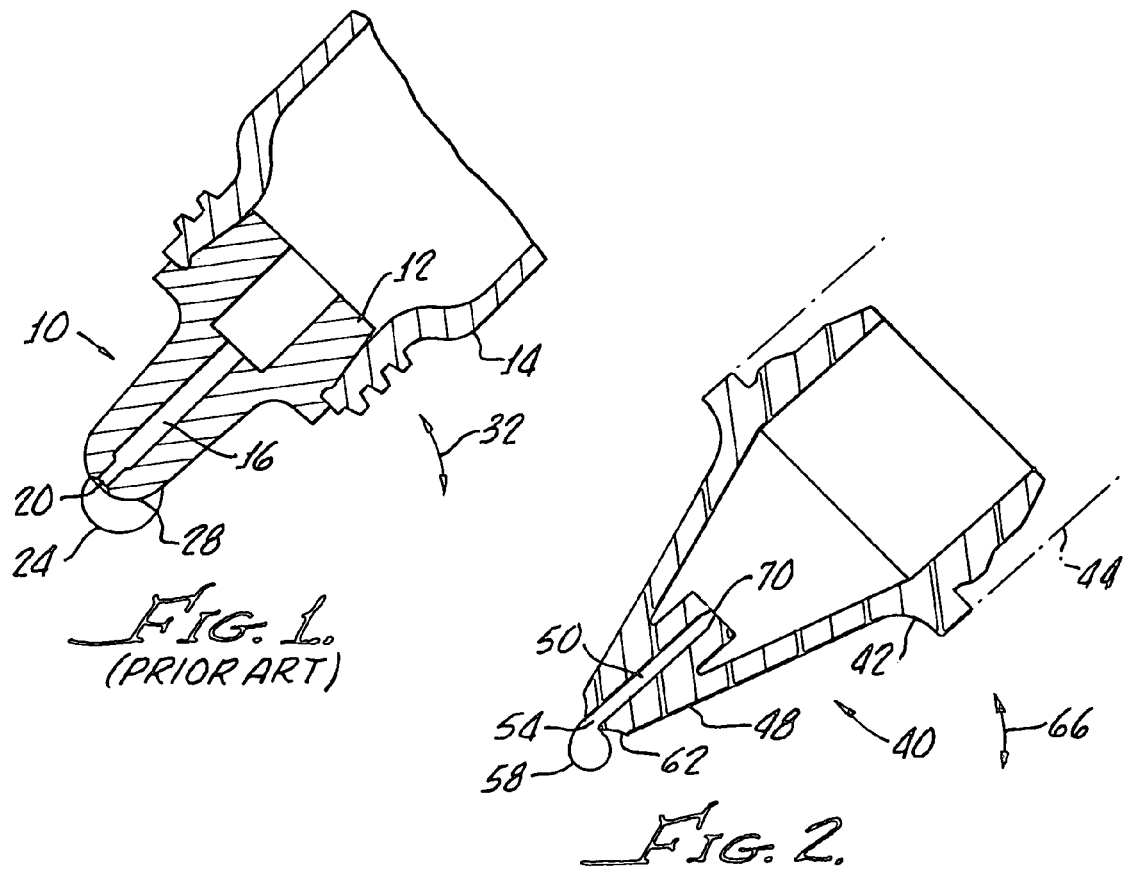
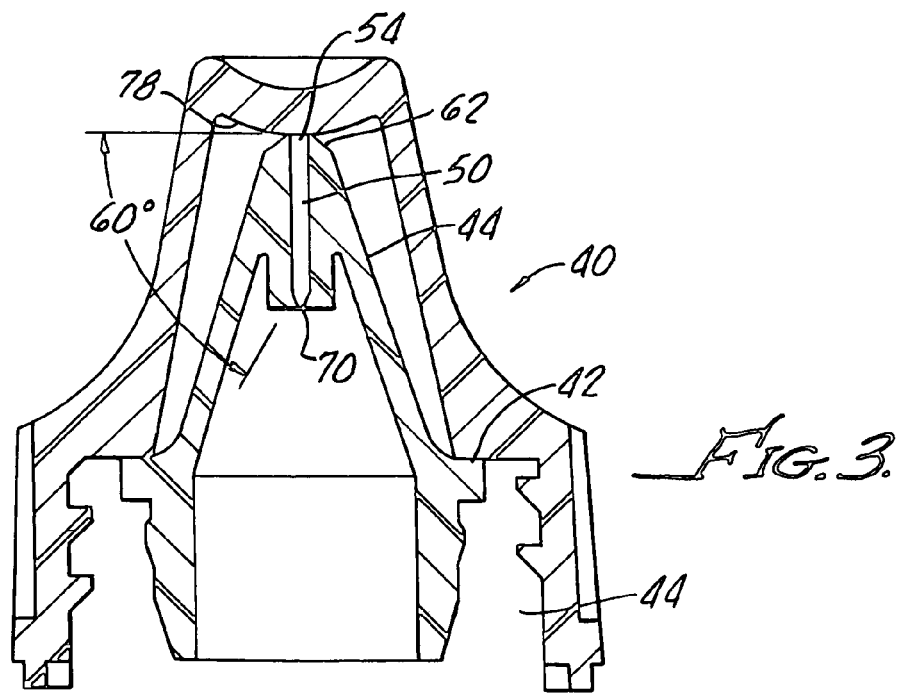

DISPENSING TIP

The present invention is generally related to a control drop dispensing system and is more particularly directed to a dispensing tip for enabling the formation of small uniform droplets of a liquid formulation.

Heretofore, many types of dispenser tips have been utilized for the purpose of transferring accurately measured small droplets of liquid.

One of the primary problems encountered with dispensing small droplets of fluid occurs as a result of the physical phenomenon of interfacial tension and surface energy. Alone or in combination, these two phenomenon (if they can be differentiated) cause a droplet being forced out of the dispenser tip to enlarge in size until it is of a weight to overcome the work of adhesion between the liquid and the dispenser surface.

Droplet size is dependent upon many factors and is often larger than the amount of liquid formulation desired to be dispensed.

A number of dispensing tips have been designed to provide small droplets to separate off the tip of a dispenser without a great deal of success.

The present invention provides for dispensing tip providing the uniform droplet formation without an elaborate nozzle/dispenser tip construction.

SUMMARY OF THE INVENTION

A dispensing tip in accordance with the present invention generally includes a body suitable for attachment to a dispensing bottle along with a nozzle having a lumen therethrough for flow of liquid formation and an egress orifice in fluid communication with the lumen for formation of the droplets.

A surface revolution surrounding the egress orifice is provided for enabling droplet separation from the egress orifice. In this manner, uniform droplet formation is effected which can be independent of dispenser tip orientation during droplet dispensing.

Preferably, the surface of revolution is a concave arcuate surface which depends from the egress orifice.

In order to further control fluid flow from the body through the lumen, an ingress orifice may be provided which is in fluid communication with the lumen for controlling passage of the liquid formulation from the dispensing bottle and into the lumen.

Preferably, the concave arcuate surface abuts the egress orifice in order to minimize surface area onto which a formed droplet can adhere.

To further enhance a sharp demarcation between the arcuate surface and the egress orifice, the arcuate surface may depend from the egress orifice and angle of about 60°.

Preferably, the egress orifice has a diameter equal to a diameter of the lumen and the ingress orifice has a diameter less than the lumen diameter.

A closure may also be provided having an inside convex depending surface for sealing the egress orifice without contact with the concave arcuate surface.

BRIEF DESCRIPTION OF THE DRAWINGS

The advantages and features of the present invention will be better understood by the following description when considered in conjunction with the accompanying drawings of which:

FIG. 1 is a cross sectional view of a prior art dispensing tip illustrating the problems of uniform droplet formation;

FIG. 2 is a dispensing tip in accordance with the present invention generally showing a body with a nozzle having a lumen therethrough, an egress orifice and a concave arcuate surface of revolution about the egress orifice which enables separation of droplets without significant contact with the nozzle in order to prevent a growing of the droplet size due to interfacial effects; and FIG. 3 is a cross sectional view of the dispensing tip shown in FIG. 2 to further illustrate a closure with an inside convex depending surface for sealing the egress orifice without contact with the concave arcuate surface.

DETAILED DESCRIPTION

With reference to FIG. 1, there is shown a prior art dispensing tip 10 including a body 12 suitable for attachment to a bottle 14 and having a lumen 16 in fluid communication with an egress orifice 20.

As illustrated, droplet formation caused by squeezing of the bottle 14 thus forcing a fluid through the lumen 16 and orifice 20 creates a droplet 24 which by either capillary or surface tension adheres to a surface 28 surrounding the egress orifice thus enabling the droplet 24 to grow in size depending upon the angular orientation of the dispensing tip 10 as indicated by the arrow 32.

With reference to FIG. 2, there is shown a dispensing tip 40 in accordance with the present invention which also includes a body 42 suitable for attachment to a bottle 44 which includes a nozzle 48 having a lumen therethrough for the flow of a liquid formulation and an egress orifice 54 in fluid communication with the lumen 50 for the formation of a droplet 58. A concave arcuate surface of revolution 62 about the egress orifice 54 enhances droplet 58 formation of uniform size independent of dispensing tip 40 orientation is indicated by an arrow 66.

With the arcuate surface 62 abutting the egress orifice 54, as more clearly shown in FIG. 3, little surface area is provided for causing droplet growth due to capillary and surface tension effects as is the case with the prior art dispensing tip 10 shown in FIG. 1.

In order to control passage of liquid formulation from a bottle 44 and through the lumen 50, an ingress orifice 70 is provided an in fluid communication with the lumen 50 with the ingress orifice 70 having a diameter smaller than a diameter of the lumen 50. As shown, the egress orifice 54 may have a diameter equal to the lumen 50 diameter.

The ingress orifice 70 prevents from over pressuring the lumen 50 with liquid formulation, thus further enhancing uniform droplet 58 formation. In that regard, the ratio of the lumen 50 diameter to the ingress orifice 70 diameter is preferably between about 3 and 4. More specifically, as an example, the lumen 50 diameter may be about 0.02 inches and the egress orifice 70 diameter may be about 0.006 inches.

In order to further enhance separation of the droplet 58 from the egress nozzle 54 without significant contact with the arcuate surface 62, the arcuate surface may be disposed and depend from the egress orifice 54 at an angle of about 60°, as illustrated in FIG. 3.

This configuration enables the dispensing tip 40 to dispense between about 10 microliters and 20 microliters of liquid formulation, preferably an ophthalmic solution into an eye (not shown).

Since with prior art devices, a typical drop size is between about 20 microliters and 50 microliters. The dispensing tip 40 enables the better control of ophthalmic solution droplet size which in turn provides for less systemic side effects from overdosing the eye and less product waste.

To further enhance droplet separation, the dispensing tip 40 may be formed with a plastic having a low surface energy, plasma treated, or coated with a low surface energy material.

As shown in FIG. 3, the dispensing tip 40 may include a closure 76 which includes an inside convex surface 78 for sealing the egress orifice 54 without contact with the concave arcuate surface 62. This arrangement prevents any contamination of the surrounding arcuate surface 62 which may further prevent adhesion of droplets 58 thereto.

Although there has been hereinabove described a specific dispensing tip in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A dispensing tip comprising:
a body suitable for attachment to a dispensing bottle;
a nozzle having a lumen therethrough for flow of a liquid formulation and an egress orifice in fluid communication with said lumen for the formation of droplets; and
a subtending concave arcuate surface of revolution about said egress orifice and depending therefrom.

2. A dispensing tip according to claim 1 wherein said egress orifice has a diameter equal to a diameter of said lumen.

3. The dispensing tip according to claim 2 further comprising an ingress orifice in fluid communication with said lumen for controlling passage of said liquid formulation from the dispensing bottle and into said lumen.

4. The dispensing tip according to claim 3 wherein said ingress orifice has a diameter smaller than a diameter of said lumen.

5. The dispensing tip according to claim 4 wherein a ratio of the lumen diameter to the ingress orifice diameter is between about 3 and about 4.

6. The dispensing tip according to claim 5 wherein the lumen diameter is about 0.02 inches and the ingress orifice diameter is about 0.006 inches.

7. The dispensing tip according to claim 1 wherein the concave arcuate surface abuts the egress orifice.

8. The dispensing tip according to claim 7 wherein the concave arcuate surface depends from said egress orifice at an angle of about 60°.

9. The dispensing tip according to claim 1 further comprises a closure with an inside convex depending surface for sealing said egress orifice without contact with the concave arcuate surface.

10. A dispensing tip comprising:
a body suitable for attachment to a dispensing bottle;
a nozzle having a lumen therethrough for flow of liquid formulation and an egress orifice in fluid communication with said lumen for formation of droplets; and
a surface of revolution subtending and surrounding said egress orifice for enhancing droplet separation from said egress orifice.

11. The dispensing tip according to claim 10 wherein said egress orifice has a diameter equal to a diameter of said lumen.

12. The dispensing tip according to claim 11 further comprising an ingress orifice in fluid communication with said lumen for controlling passage of said liquid formulation from the dispensing bottle and into said lumen.

13. The dispensing tip according to claim 12 wherein said ingress orifice has a diameter smaller than a diameter of said lumen.

14. The dispensing tip according to claim 13 wherein a ratio of the lumen diameter to the ingress orifice diameter is between about 3 and about 4.

15. The dispensing tip according to claim 14 wherein the lumen diameter is about 0.02 inches and the ingress orifice diameter is about 0.006 inches.

16. The dispensing tip according to claim 10 wherein the surface of revolution abuts the egress orifice.

17. The dispensing tip according to claim 16 wherein the surface of revolution depends from said egress orifice at an angle of about 60°.

18. The dispensing tip according to claim 17 wherein the surface of revolution is arcuate and depends from said egress orifice.

19. The dispensing tip according to claim 18 further comprising a closure with an inside convex depending surface for sealing said egress orifice without contact with the concave arcuate surface.

* * * * *